United States Patent
Dal Farra et al.

(10) Patent No.: US 8,309,144 B2
(45) Date of Patent: Nov. 13, 2012

(54) USE OF A CRUCIFEROUS PROTEIN HYDROLYSATE AS A DEPIGMENTATION AGENT OR FOR A COSMETIC AND/OR PHARMACEUTICAL COMPOSITION

(75) Inventors: Claude Dal Farra, Kerhonkson, NY (US); Nouha Domloge, Valbonne (FR); Dominique Peyronel, Marseilles (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 12/979,735

(22) Filed: Dec. 28, 2010

(65) Prior Publication Data

US 2011/0158926 A1    Jun. 30, 2011

Related U.S. Application Data

(60) Continuation-in-part of application No. 12/854,334, filed on Aug. 11, 2010, now abandoned, which is a division of application No. 11/578,507, filed as application No. PCT/FR2005/000985 on Apr. 21, 2005, now abandoned.

(30) Foreign Application Priority Data

Apr. 21, 2004  (FR) ...................................... 04 04192

(51) Int. Cl.
*A61K 36/31*    (2006.01)
(52) U.S. Cl. ......................................................... 424/755
(58) Field of Classification Search ........................ None
See application file for complete search history.

(56) References Cited

U.S. PATENT DOCUMENTS 4,054,677 A  * 10/1977  Orban ........................... 426/602
4,959,350 A    9/1990  Frokjaer et al.
2004/0067279 A1  4/2004  Delest et al.

OTHER PUBLICATIONS

Jenkins et al. "Influence of Triglycerides and Free Fatty Acids in Milk Replacers on Calf Performance, Blood Plasma and Adipose Lipids". J Dairy Sci vol. 68, No. 3 (1985) pp. 669-680.*

* cited by examiner

*Primary Examiner* — Amy L Clark
(74) *Attorney, Agent, or Firm* — Young & Thompson

(57) ABSTRACT

The use of an effective quantity of a protein hydrolysate from plants belonging to the crucifer family, as whitening and/or depigmenting skin agent, for the preparation of a cosmetic and/or dermatological and/or pharmaceutical composition. In a preferred embodiment, the hydrolysate is obtained from rapeseed proteins. Also the composition may contain the aforementioned hydrolysate in a cosmetically and/or pharmaceutically acceptable excipient chosen between glycerol, propanediol and butylene glycol.

9 Claims, 3 Drawing Sheets

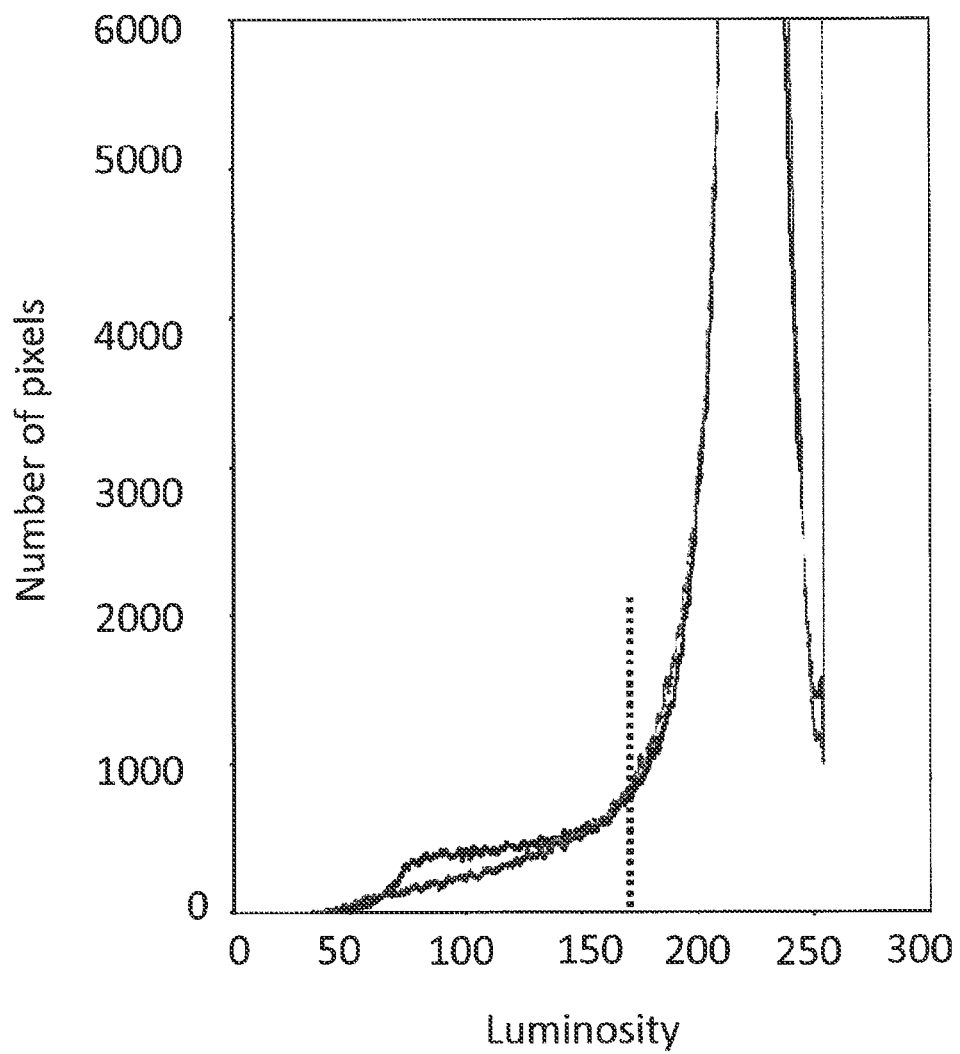
*Fig. 1a: Placebo*: black
*1 % Arbutin*: grey
Evaluation of the whitening effect of a non fermented rapeseed peptide hydrolysate on the skin: *in vitro* study

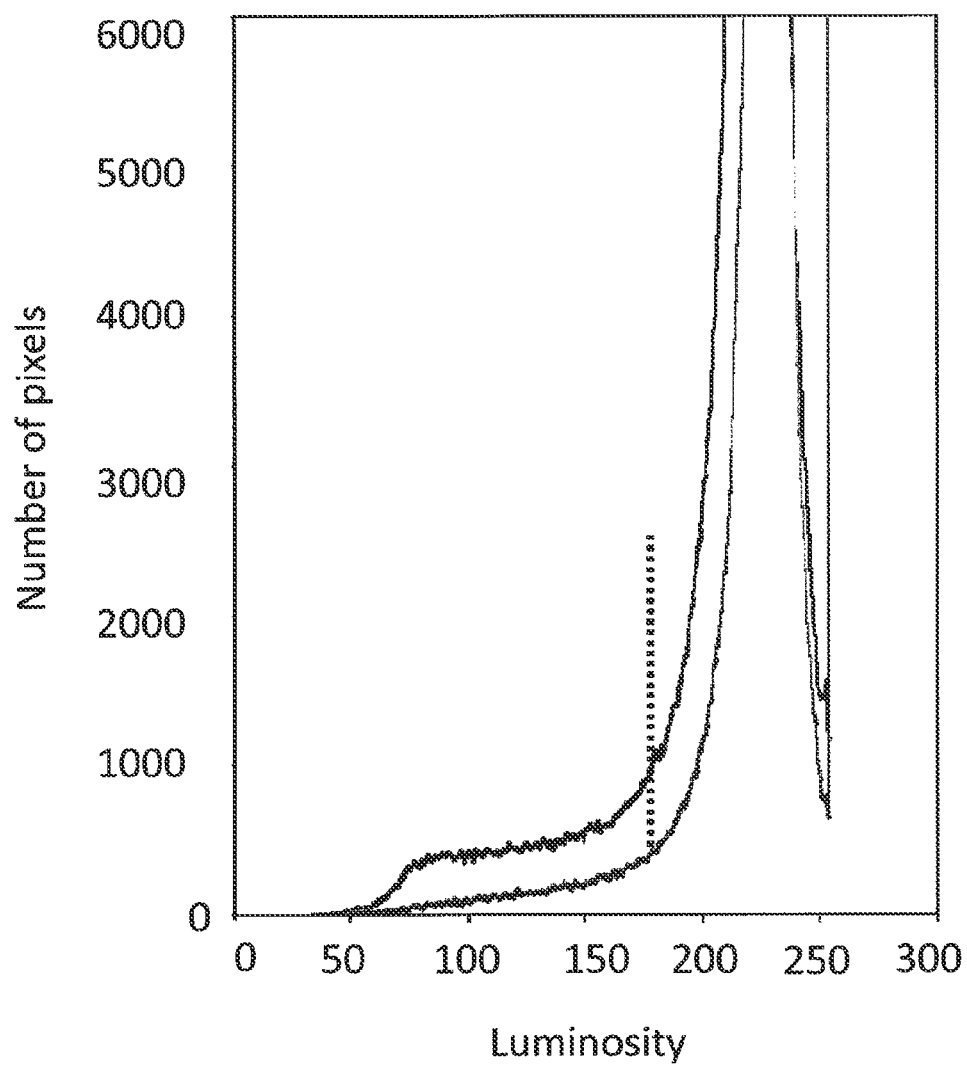
*Fig. 1b: Placebo*: black
*1 % Rapeseed*: grey
Evaluation of the whitening effect of a non fermented rapeseed peptide hydrolysate on the skin: *in vitro* study

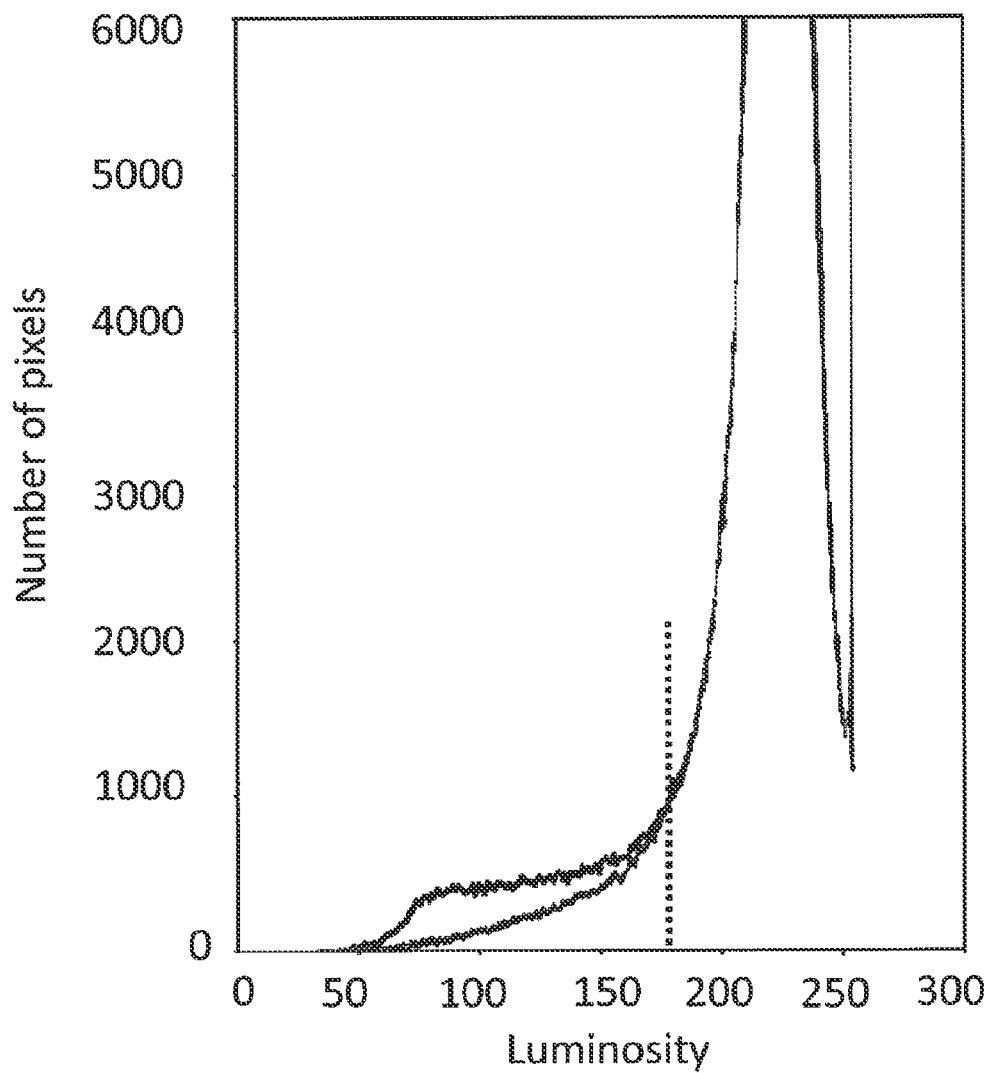
*Fig. 1c: Placebo*: black
*1 % Rapeseed/0,5% Arbutin*: grey
Evaluation of the whitening effect of a non fermented rapeseed peptide hydrolysate on the skin: *in vitro* study

USE OF A CRUCIFEROUS PROTEIN HYDROLYSATE AS A DEPIGMENTATION AGENT OR FOR A COSMETIC AND/OR PHARMACEUTICAL COMPOSITION

This application is a continuation-in-part of co-pending application Ser. No. 12/854,334 filed on Aug. 11, 2010, which is a division of application Ser. No. 11/578,507 filed on Oct. 16, 2006, which is the 35 U.S.C. §371 national stage of International PCT/FR2005/000985 filed on Apr. 21, 2005, which claims priority to French Application No. 04 04192 filed on Apr. 21, 2004. The entire contents of each of the above-identified applications are hereby incorporated by reference.

The invention relates to the cosmetic and pharmaceutical fields, and, in particular, the field of dermatology. The present invention has as an aim the use of an effective quantity of a protein hydrolysate from plants belonging to the crucifer family, as a whitening or skin depigmenting agent and/or, in or for the preparation of a cosmetic and/or dermatological and/or pharmaceutical composition.

The color of the skin and hair of mammals is under the influence of various factors. These include genetic factors, of course, but also environmental ones such as, for example, sun exposure. Skin color rests primarily on the presence of a particular pigment, melanin. Indeed, melanin plays a fundamental role in the determination of the color of the skin. It is synthesized by broad dendritic cells called melanocytes, which are located at the dermal-epidermal junction. Melanin exists in two different forms: phaeomelanin, which is a yellow pigment, and eumelanin, which is black in color. The various proportions and sizes of these pigments, as well as carotenoids and the microcirculation of the blood, give the skin its great diversity of color.

Both types of melanin are synthesized from the same amino acid, tyrosine. This synthesis depends upon a key enzyme, tyrosinase, which transforms tyrosine into DOPA, and then into DOPA-quinone. DOPA-quinone gives rise to phaeomelanin or eumelanin. In the presence of cysteine, an amino acid rich in sulfur, DOPA-quinone transforms into Cysteinyl-DOPA, an intermediate of phaeomelanin synthesis; while in the absence of cysteine, indol-5, 6-quinone is formed and eumelanin is synthesized. Melanocytes then transfer the melanin to the adjacent cells, the keratinocytes.

The production of melanin, as well as its transport, are controlled by various factors such as UV radiation, hormones, and chemicals. Thus, an increase in UV radiation exposure causes pigment synthesis and results in a darkening of the skin. Disturbances of the pigmentation, more or less benign, can appear. They appear, for example, as freckles, beauty marks, diffuse marks such as pregnancy marks, chloasma, and as other hyperpigmentary disorders such as lentigo. Moreover, aging can modulate cutaneous pigmentation. Thus, some people can see skin marks appear, more or less dark or colored, given as zones of heterogeneous coloration that form senescence marks.

The use of melanin synthesis inhibitors or regulators as well as any other depigmenting and/or whitening product, is thus of particular interest in the fields of cosmetology and/or dermatology. This use is not only interesting when a genuine skin depigmentation is sought, as in the case of the whitening of strongly pigmented skin or with the inhibition of hyperpigmented cutaneous zones that result in an unaesthetic appearance of the skin; but it is also the case in certain applications which aim at enhancing the complexion, by increasing the luminosity of the skin and the brilliance of skin surface tissues.

To date, many molecules have been proposed but very few are actually used, many of them presenting irritation problems and even toxicity problems. Among these molecules, one can reference phenol derivatives such as hydroquinone and resorcinol, which inhibit a series of reactions of L-tyrosine conversion to melanin by inhibiting tyrosinase activity (Takano, 1984). One can also reference L-ascorbic acid and its derivatives, magnesium ascorbyl acetate, kojic acid, and lactic acid. New products and molecules have been developed in order to solve these problems. For instance, document GB 1349955 describes a whitening composition containing hydroquinone, a scaling agent, and a corticosteroid anti-inflammatory drug. Document EP98401360 describes the use of sulfites and metal sulfites in a cosmetic composition with a depigmenting activity.

A certain number of substances introduced into cosmetic and medicinal products have thus emerged. There still remains, however, progress to be made in order to regulate the abovementioned problems in a satisfactory manner. There remains, in particular, the need for a depigmenting and/or whitening composition that, although being suitably tolerated by the skin, is more effective than the compositions previously listed.

For the inventors, the technical problem to solve was thus to find a new cosmetically or pharmaceutically acceptable substance, which possessed a genuine whitening and/or depigmenting activity on the skin without undesirable side effects such as toxic reactions or cutaneous irritation.

The inventors succeeded in selecting specific substances which present remarkable properties when applied to the skin. In particular, the inventors discovered that a protein hydrolysate from plants belonging to the crucifer family has remarkable properties on the skin and, more particularly, whitening properties. This compound makes it possible, indeed, to significantly inhibit melanin synthesis in cutaneous cells.

Plants of the crucifer family (Cruciferae) form a broad family of approximately 3200 species divided into 375 genera throughout the world. Crucifers are also called *Brassicaceae*. These plants are found mainly in temperate areas of the Northern Hemisphere and, more particularly, in the areas surrounding the Mediterranean. Crucifers take their name from the position of their sepals and petals, which form a cross. Crucifers are herbaceous plants and are perennial, annual, and often bi-annual. Their root swivel and is tuberous. The foliage is alternate, with reduced and deciduous stipules, which may even be absent. The fruit is a silique, its form, its length, and its thickness are used to recognize the species. The seeds detach gradually; they are deprived of endosperm, the reserves being primarily of lipidic origin. Among this family we can cite large oleaginous crop plants, such as rape (*Brassica napus*, var. *oleifera*); food plants including all the varieties of "cabbage" (*Brassica* genus); condiments such as mustard (*Sinapis* genus); and plants with decorative interest such as wallflowers and yellow alyssum (*Alyssum* genus).

In previous documents, cosmetic compositions containing *Brassicaceae* extracts have already been proposed. Thus, for example, patent FR 2802417 describes a cosmetic and/or pharmaceutical preparation containing an effective quantity of an extract of *Brassicaceae* and a fat substance and/or emulsifiers. Moreover, another patent application FR 2 904 555 describes a cosmetic and/or pharmaceutical composition containing an effective quantity of a rapeseed extract as a pigmenting agent. However, to the knowledge of the applicant, what has never been described in prior art is a composition containing a cosmetically and/or a pharmaceutically acceptable excipient chosen between glycerol, propanediol and propylene glycol, and a peptide hydrolysate from rape seed proteins, and the method of whitening and/or depigmenting of the skin and/or the hair in need. Indeed, in the prior art FR 2 904 555, the process used to obtain this hydrolysate is simpler than the one used in the present invention, and as a consequence, the hydrolysate according the present invention is totally different from the one obtained in prior art.

Thus, according to a first aspect, the present invention has as an aim the use of an effective quantity of a protein hydrolysate from plants belonging to the crucifer family as a whitening active ingredient in or for the preparation of a cosmetic and/or dermatological and/or pharmaceutical composition. According to a highly preferred embodiment of the invention, the hydrolysate is a hydrolysate of non fermented proteins from plants belonging to the crucifer family, and more preferably from rape (*Brassica napus*).

FIG. 1 shows histograms of the luminosity of isolated regions treated with a placebo, or arbutin, or a non fermented rapeseed peptide hydrolysate, or a combination of both.

In a first embodiment, the composition according the invention contains, in a cosmetically and/or pharmaceutically acceptable excipient, at least a peptide hydrolysate from rapeseed, characterized in that the excipient is chosen between glycerol, propanediol, and propylene glycol.

The term "hydrolysate" indicates any substance having undergone hydrolysis. Hydrolysis is defined as the splitting of a molecule by a water molecule. Hydrolysis can be enzymatic or chemical. Preferentially, according to the invention, hydrolysis is enzymatic. A protein or peptide hydrolysate thus indicates the product obtained after the hydrolysis of plant proteins. The hydrolysis of proteins, more or less processed, makes it possible to obtain a hydrolysate containing either peptides of variable molecular weights, or amino acids. The proteins thus hydrolized were examined for their properties in the fields of cosmetics and dermatology. In the present invention, we will use indifferently the term peptide or protein hydrolysate.

In a first embodiment, the protein hydrolysate is prepared from fermented proteins, i.e. from proteins which have undergone a stage of fermentation. By fermentation, we understand a transformation of the organic substances under the action of microorganisms. Preferentially, according to the invention, the microorganisms used are yeasts, and more particularly yeasts of the *Rhizopus, Aspergillus*, or *Penicillium* genus. Nevertheless, in a preferred embodiment, the peptide hydrolysate is obtained from non fermented rapeseed proteins, i.e. from proteins which not have undergone a stage of fermentation.

The protein hydrolysate from plants belonging to the crucifer family is to be understood as a hydrolysate at least from a plant belonging to the crucifer family. Of course, this hydrolysate can be prepared, at least, from any of the many genera and species belonging to the crucifer family. According to the invention, the plant used in order to obtain the hydrolysate of fermented or non fermented proteins, belonging to the crucifer family, is rape (*Brassica napus*). Preferentially, the protein hydrolysate from plants belonging to the crucifer family is obtained from the seed of these plants. Thus, according to a preferred method of embodiment of the invention, the protein hydrolysate is obtained from rapeseed.

FIRST EMBODIMENT

Process for Obtaining a Peptide Hydrolysate from Fermented Rapeseed Proteins Any method of extraction or purification known by the person skilled in the art can be used in order to prepare the hydrolysate according to the invention. One can, for example, in a first stage, delipidate crucifer seeds, such as rapeseed, by a simple pressing and/or the action of a traditional organic solvent (such as an alcohol, a hexane, or acetone). After the drying of the product thus obtained, one obtains a protein-enriched residue commonly called "oil cake." A fermentation stage, then, is advantageously carried out from this oil cake.

According to another technique, one can envisage performing an extraction of a protein fraction obtained from this oil cake, this protein fraction will then be used as substrate for fermentation. Protein extraction stage is carried out in aqueous, neutral, or basic medium. Preferentially, according to the invention, protein extraction will be carried out in aqueous medium, slightly basic, and at hot temperature. The proteins will be collected by precipitation or concentration.

The fermentation stage is carried out preferably with yeasts, and preferentially with yeasts of the *Rhizopus, Aspergillus*, or *Penicillium* genus. In the fermentation medium, the rapeseed extract, a source of nitrogenous matter, is supplemented with sugars (glucoses) as well as by various elements necessary to the growth of yeasts, including amino acids and mineral salts. A low glycerol or alcohol concentration can be added. The culture is carried out in a fermentor under slow stirring (10 to 60 rpm), at a temperature between $20°$ C. and $40°$ C. and with a pH varying from 5 to 7.5, the air flow being constant. The duration of this stage is highly variable; indeed, it can vary from twelve hours to twenty days. The culture medium, thereafter, is subjected to a heat treatment, at a temperature between $80°$ C. and $135°$ C.

The final stage of protein hydrolysis is carried out by proteases of vegetable origin such as papain or bromelaine; or by enzymes termed "industrial" such as alcalase, flavourzyme, etc. The culture medium thus hydrolized is centrifuged and filtered until a fermented protein hydrolysate of crucifers is obtained.

This hydrolysate is solubilized in one or more solvents. One can cite aqueous solvents in particular. By aqueous solvent, we understand any solvent made up completely or partially of water. One can cite water itself, hydroalcoholic solvents in all proportions, and solvents consisting of water and a compound such as propylene glycol or butylene glycol in all proportions.

SECOND EMBODIMENT

Process for Obtaining a Peptide Hydrolysate from Non Fermented Rapeseed Proteins Rapeseed (*Brassica napus*) is dissolved in 10 volumes of water in the presence of 2% Polyclar® 10 (polyvinylpyrrolidone-PVPP-insoluble). The mixture is adjusted to a pH between 6 and 8 with an aqueous solution of sodium hydroxide 1 M.

After pH adjustment, it is added 2% bromelain in the reaction medium. The hydrolysis was obtained after stirring for 2 hours at $50°$ C. We proceed to the inactivation of the enzyme by heating the solution at $80°$ C. for 2 hours. After centrifugation, the aqueous solution corresponding to the rapeseed extract is recovered.

The purification process begins by successive filtrations using filter plates-Seitz Orion decreasing porosity (up to 0.2 microns) to obtain a solution bright and clear. At this stage, the rapeseed extract is characterized by dryness of 30-40 g/kg, a proteins rate of 25-35 g/L and a sugars rate of 2-5 g/L.

The nature of this protein extract was demonstrated by polyacrylamide gel electrophoresis. For this analysis, we used the gel NuPAGE® Bis-Tris Pre-cast (Invitrogen). Under these conditions, we see three major protein families: the first family corresponds to protein molecular weight from 65 to 35 kDa, the second family of proteins of 25-15 kDa and the last family to lower molecular weight proteins to 5 kDa.

This solution is then purified by eliminating high molecular weight proteins using tangential flow filtration.

For this, the rapeseed solution is pumped under pressure through support Pellicon® equipped cassette Pellicon® 2 Biomax 50 kDa. This first filtrate is recovered and is then filtered through a second cassette Pellicon® 2 Biomax 10 kDa. It is then retrieved a second filtrate which eluted through one more tape Pellicon® 2 Biomax 5 kDa. At the end of purification, a yellow-orange, bright and clear plant extract is obtained from rapeseed. It is characterized by a dryness of 6-8 g/kg, a protein rate of 3.5-6 g/L and a sugar rate of 1-2 g/L.

This solution is then analyzed by high pressure liquid chromatography using a HP1100 apparatus controlled by the ChemStation software. The column used during the elution of the extract of rape is a Nucleosil 300-5 C4 PN® (125×4 min). This column chromatograph allows proteins with molecular weights of 0.2 to 25 kDa (a gradient of solvents). Under these chromatographic conditions, it has been isolated several peptide fractions. These various fractions were analyzed by mass spectrometry to identify their molecular peaks. Finally, it was revealed the presence of a peptide fraction of really low molecular weight (between 400 and 700 Da) rich in proline amino acid.

This peptide hydrolysate of non fermented proteins is solubilized in a cosmetically or pharmaceutically acceptable excipient chosen between glycerol, propanediol and propylene glycol. In a preferred embodiment, the excipient is glycerol.

The hydrolysates of fermented protein of plants belonging to the crucifer family are analyzed for their content of protein components. We refer, by components of a protein nature, to protein fragments, peptides, and free amino acids present in the mixture. The peptides, amino acids, and protein fragments are measured out according to standard techniques, well-known by specialists of the profession. Thus, according to an advantageous embodiment of the invention, the hydrolysate contains a quantity of components of protein nature representing between 30% and 90% of the total weight of the dry matter. More particularly, this quantity ranges between 50% and 80% of the total weight of the dry matter. Moreover, the peptide hydrolysate of non fermented proteins contains 3.5 to 6 g/l of peptides and has a concentration in sugars comprised between 1 and 2 g/l. Finally, it contains peptides having a molecular weight comprised between 400 and 700 Da and is rich in proline amino acid.

The invention has, moreover, as an aim, the use of an effective quantity of a protein hydrolysate from plants belonging to the crucifer family, such as previously defined, in or for the preparation of a composition; the extract or the composition being intended for depigmentation and/or whitening and/or lightening of the skin. According to the invention, the protein hydrolysate from plants belonging to the crucifer family is a hydrolysate of fermented proteins, i.e. proteins processed by a fermentation stage. In a highly preferred embodiment, the peptide hydrolysate from rapeseed is a hydrolysate of non fermented proteins, i.e. proteins processed with no fermentation stage.

The active ingredient according to the invention, or the composition containing it, will enable the skin to lighten, or even to whiten. From the start, the skin has the capacity to be more or less colored and more or less dark; this color having a natural origin, and it is under the influence of external factors such as UV radiation and age. In addition, the active ingredient according to the invention, or the composition containing it, will allow for, in a more or less direct manner, the disappearance of pigmentary marks of the skin and/or the depigmentation of hair. It will thus make it possible to lighten the hyperpigmented areas, i.e. the cutaneous zones containing a great quantity of melanin. By pigmentary marks of the skin, we understand all the modifications of skin pigmentation resulting in a general darkening or a local darkening, thus forming more or less dark marks. These modifications can be of natural origin or induced by various agents such as UV radiation and chemicals. These pigmentary disorders can appear as freckles, beauty marks, diffuse marks such as pregnancy marks, chloasma, as well as other hyperpigmentary disorders such as lentigo. Disturbances of this pigmentation, more or less benign, can also appear naturally with aging. Certain people can thus see marks appearing on the skin more or less dark and/or colored, given as zones of heterogeneous coloration that form senescence marks. More generally, the hydrolysate according to the invention makes it possible to control cutaneous pigmentation.

The active ingredient, according to the invention, is an efficient whitening or depigmenting active ingredient which acts, among other ways, by inhibiting the formation of melanin in melanocytes. Thus, according to another aspect, the invention relates to the use of a hydrolysate of fermented protein from plants belonging to the crucifer family, such as previously defined, in or for the preparation of a composition, in order to inhibit and/or to decrease tyrosinase activity, and/or in order to inhibit and/or to decrease melanin synthesis. In a particular embodiment, the invention relates to a method for depigmentation and/or whitening and/or lightening of the skin and/or the hair, comprising administering to said skin and/or hair in need of treatment thereof an effective amount of a composition comprising a cosmetically or a pharmaceutically acceptable excipient chosen between glycerol, propanediol and butylene glycol, and a peptide hydrolysate from rapeseed as whitening and/or depigmenting active ingredient. In a more particularly embodiment, the hydrolysate is obtained from non fermented rapeseed proteins. Moreover, the method is aimed to remove or decrease skin pigmentary marks, and inhibit and/or decrease melanin synthesis of cutaneous cells.

The invention has for another object a composition containing as an active ingredient, in a cosmetically or pharmaceutically acceptable medium, a protein hydrolysate from plants belonging to the crucifer family such as previously defined. According to a first embodiment of the invention, the composition contains a hydrolysate of fermented proteins from plants belonging to the crucifer family.

The invention relates to a cosmetic and/or dermatological composition containing a depigmenting active ingredient as well as its use in order to obtain skin lightening or to treat pigmentary marks. The composition according to the invention can be a cosmetic and/or dermatological and/or pharmaceutical composition. Preferentially, according to the invention, the composition is a cosmetic composition, because it is intended to improve the appearance and the general cutaneous performance of the individual who uses it. More particularly, this composition is adapted to a use with the aim of optimizing whitening and/or bleaching of the skin, hair depigmentation, and treatment of pigmentary marks of the skin. The composition according to the invention is preferentially a cosmetic and/or dermatological composition adapted for cutaneous topical administration including a cosmetically or dermatologically acceptable medium. It is obvious that the invention is addressed to mammals in general and to human beings in particular.

The effective quantity of active ingredient corresponds to the quantity necessary in order to obtain the desired result. According to an advantageous embodiment of the invention, the abovementioned protein hydrolysate is present in the compositions of the invention at a concentration ranging from 0.0001% to 20% approximately, and preferentially with a concentration ranging from approximately 0.01% to 10%, compared to the total weight of the final composition.

According to an advantageous embodiment of the invention, the abovementioned hydrolysate is solubilized beforehand in one or more cosmetically or pharmaceutically acceptable solvents like water, ethanol, propanol or isopropanol, propylene glycol, butylene glycol, dipropylene glycol, ethoxylated or propoxylated diglycols, or any mixture of these solvents. According to a highly preferred embodiment, the hydrolysate is a non fermented protein hydrolysate from rapeseed, solubilized in a cosmetically or pharmaceutically acceptable excipient chosen between glycerol, propanediol and propylene glycol. Preferably, the excipient is glycerol. According to another advantageous embodiment of the invention, the abovementioned hydrolysate is solubilized beforehand in a cosmetic or pharmaceutical vector such as liposomes, or adsorbed on powdery organic polymers or on mineral supports like talcs and bentonites, and, more generally, solubilized in or fixed on any cosmetically or pharmaceutically acceptable vector.

Whatever the form of the invention, the composition according to the invention can be introduced, injected, or applied to the skin (on any cutaneous area of the body), hair, nails, or mucous membranes. According to the mode of administration, the composition according to the invention can be in all the galenic forms normally used. Preferentially, the compositions according to the present invention will be in a galenic form adapted for cutaneous topical administration including a cosmetically or dermatologically acceptable medium. They cover all the cosmetic and dermatological forms. These compositions must contain an acceptable cosmetic or dermatological medium. That is to say, a medium that is compatible with the skin, hair, and nails.

These compositions can take the form of an aqueous, hydroalcoholic, or oil solution; or the form of oil-in-water emulsions, water-in-oil emulsions, or multiple emulsions. They can also be used as creams, suspensions, or powders adapted for application to the skin, mucous membranes, lips, and/or hair. These compositions can also be more or less fluid or solid and can take the form of creams, lotions, milks, serums, ointments, shampoos, gels, pastes, and mousse. They can also take a solid form like a stick, or be applied to the skin in the form of aerosols. They can also be used as a skin care product and/or as makeup for the skin.

In all cases, one skilled in the art will carefully consider the selection of additives, as well as their proportions, so as not to compromise the advantageous properties of the composition relating to the invention. These additives can, for example, correspond to 0.01% to 20% of the total weight of the composition. When the composition according to the invention is an emulsion, the fatty phase can represent 5% to 80% of the weight, but preferably it would represent 5% to 50% of the weight with respect to the total weight of the composition. Emulsifiers or co-emulsifiers used in the composition will be selected from among those that are standardly used in the domain under consideration. For example, they can be used in a proportion of 0.3% to 30% of the weight relative to the total weight of the composition. Of course, the person skilled in the art should select the complementary compounds for the composition, active or non-active, as well as the amounts of the complementary compounds in such a way that the advantageous properties of the composition will not be perceptibly altered by the envisioned addition.

According to the invention, the compositions find an application in particular as a cosmetic or pharmaceutical composition for the skin, but also as a cosmetic composition for the hair. They find a very particular application as a skin and/or hair depigmentation and/or bleaching product. According to the invention, the composition can also be a composition making it possible to fight against pigmentary marks of the skin.

According to the invention, one can add to the composition, among other things, various active agents particularly intended for the prevention and/or the treatment of pigmentary disorders. Moreover, according to the invention, the composition can associate the previously defined protein hydrolysate with other active agents supporting its action. Thus, it can be added to active agents having a keratolytic action, i.e. scaling agents with an exfoliating action, such as alpha-hydroxyacids and beta-hydroxyacids. These agents operate efficiently on the mechanisms of pigmentation.

According to another aspect, according to the invention, the composition can be a solar composition, i.e. a composition contributing to protection against sun radiation. Thus, according to the invention, active ingredient contributing to sun protection, such as solar filters, can advantageously be added to the composition.

The compositions, which are the object of the invention, find their application particularly in the vast number of cosmetic and dermatological treatments. They can form a cosmetic composition particularly for the treatment, protection, care, and makeup removal and/or cleaning of the skin and/or hair, and/or for the makeup of the skin, lips, lashes and/or body. According to the invention, the composition can also consist of solid preparations which also include soaps and cleansing soap bars. The composition can also be conditioned in the form of a composition for aerosol which also includes a pressure-induced propelling agent.

According to another aspect, the present invention relates to a cosmetic treatment process intended to lighten the skin and/or hair. The invention also relates to a cosmetic treatment process intended to treat skin pigmentation disorders. These skin and/or hair cosmetic treatment processes consist in applying to the surface of the skin, or on the hair, an effective quantity of a protein hydrolysate from plants of the crucifer family, such as those previously defined, in order to obtain the desired action. Preferentially, the process consists in applying to the surface of the skin, or on the hair, an effective quantity of a fermented protein hydrolysate from plants of the crucifer family, such as those previously defined.

The particular modes of embodiment of this cosmetic treatment process also result from the previous description. The invention's process of cosmetic treatment can be implemented in particular by applying the cosmetic compositions defined above, according to the technique of customary use of these compositions; for example: application of creams, gels, serums, lotions, milks, shampoos, or anti-solar compositions on the skin or the hair, or, application of toothpaste on gums.

Other advantages and characteristics of the invention will become apparent by reading the following illustrative and unrestrictive examples.

EXAMPLE 1

Preparation of Fermented Protein Hydrolysate from Plants Belonging to the Family of Crucifers In a first stage, 1 kg of rapeseed is delipidated by the action of an organic solvent, hexane. After drying the product, one obtains a protein-enriched residue (the oil cake). A fermentation stage is then carried out.

The culture medium of fermentation is made of:
a rapeseed oil cake at a concentration of 18 g/l,
glucose at a concentration of 20 g/l,
sodium chloride at a concentration of 4 g/l,
$K_2HPO_4$ at a concentration of 2 g/l.

The pH of this medium is 6.5. It is seeded with yeasts of the *Rhysopus* genus. The culture is carried out in a fermentor, under slow stirring (30 rev/minute), at 30° C., for 24 hours. The mixture is then put in the autoclave for twenty minutes at 120° C., and then hydrolized by the addition of an enzyme, papain, at 60° C. for 4 hours under stirring. Then this mixture is heated at 80° C., is centrifuged and filtered until a limpid solution is obtained. Then it is concentrated under vacuum, and then filtered again on filter plates and then on a sterilizing cartridge.

A hydrolysate of brown color is then obtained with a 30 g/l titration of protein compounds. That is to say, we obtain a hydrolysate containing a quantity of compounds of protein nature representing approximately 65% of the total weight of the dry matter. This hydrolysate is then solubilized in a solution of dipropylene glycol.

One can, however, carry out a protein fraction extraction stage on the oil cake before fermentation; this protein fraction will then be used as substrate for fermentation. This extraction is carried out using an aqueous, basic solution (at pH 11) and at hot temperature (50° C.), under constant stirring for one hour. The extraction medium is then brought towards a pH of 3 or 4, by an acid solution, preferentially by a mineral acid (hydrochloric or sulfuric acid). A precipitate of protein nature is formed and is collected by centrifugation followed by filtration. The mixture is put in suspension again to be used as a substrate for fermentation.

EXAMPLE 2

Demonstration of the Depigmenting Effect of the Extract from Example 1 Using Ex Vivo Tests The depigmenting activity of the hydrolysate according to example 1 was shown in skin samples.

Biopsies of 6 mm in diameter are taken from samples of human skin. These biopsies are maintained in ex vivo culture in the presence of a specific medium (DMEM 1 g/L, HAMF12, SVF, and antibiotics) on inserts deposited in 6-well plates. The biopsies are then treated with the active ingredient at a concentration of 1% following various conditions. Controls, that is to say, tests on biopsies without the application of the active ingredient, are also carried out for each condition.

Condition A: the active ingredient is applied for 5 days, at a rate of 2 applications per day.
Condition B: a skin irradiation of 100 mJ/cm² is carried out; the active ingredient is then applied twice over a 24-hour period.
Condition C: a pretreatment with the active ingredient is carried out over a 24-hour period (2 applications), followed by 4 days of culture without application, then an irradiation of 100 mJ/cm² is carried out, the active ingredient is then applied twice over a 24-hour period.
Condition D: a pretreatment with the active ingredient is carried out over a 24-hour period (2 applications), followed by an irradiation of 100 mJ/cm², the active ingredient is then applied over a 2-day period (2 applications).
Condition E: a pretreatment with the active ingredient is carried out over a 24-hour period (2 applications), followed by an irradiation of 100 mJ/cm², the active ingredient is then applied over a 5-day period (2 applications).

A quantitative evaluation of the presence of melanin in the epidermis of the skin samples is carried out histologically, under an optical microscope, using the Fontana-Masson staining method.

The skin biopsies are embedded into paraffin and 4 µm-histological sections are carried out. These sections are then stained using the Fontana-Masson technique: the slides are deparaffinized, hydrated, and then treated with ammoniacal silver solution. After two minutes in the microwave, the slides are rinsed, treated with sodium thiosulfate, are rinsed again, and then counter-stained with hematoxylin before being dehydrated and placed under cover glasses, thus allowing visualization, by optical microscopy, of the melanin present in the epidermis.

Visualization of melanin amount using an optical microscope made it possible to count three types of skin pigmentation:
(+): Strongly pigmented skin, i.e. skin presenting significant melanin content (homogeneous deposit).
(−): Fairly pigmented skin, i.e. skin presenting moderate melanin content (scattered spots of melanin, nonhomogeneous deposit).
(− −): Skin slightly pigmented or not pigmented.

The results are gathered in the table below:

| Conditions: | Without active ingredient | With active ingredient |
| --- | --- | --- |
| A | − | − − |
| B | + | − |
| C | + | − − |
| D | + | − |
| E | + | − − |

These results enable us to conclude that in the absence of UVB irradiation (condition A), the active ingredient decreases the rate of melanin in comparison with samples of untreated skin. In addition, melanin synthesis induced by UVB irradiations is attenuated when the active ingredient is applied for 2 to 5 days after irradiation. This effect is even more noticeable when the samples are pretreated with the active ingredient before irradiation. Thus, the active ingredient, according to the invention, makes it possible to significantly decrease skin pigmentation and likely enables an inhibition of melanin synthesis.

EXAMPLE 3

Demonstration of the Depigmenting Effect of the Extract of Example 1 by a Clinical Study (In Vivo Tests)

1. Principle of the Test

An in vivo test was carried out on volunteers in order to show the depigmenting effect of the hydrolysate according to example 1. This test was carried out by studying the melanin index of the cutaneous surface as well as through an analysis of the zones of the skin treated with the active ingredient.

2. Experimental Model

A clinical study was carried out on a group of 15 volunteers, age 45 to 76. This study was carried out as a double-blind test against placebo; the volunteers had a nonhomogeneous skin pigmentation (i.e. pigmentary marks) due to age and/or UV exposure. The volunteers applied the active ingredient, formulated in a 3% composition, on a delimited area of the forearms, at a dose of 2 mg/cm², with another area receiving the placebo. This application was carried out twice a day for 4 weeks.

The depigmenting effect was measured by a quantification of the melanin index carried out using a specific instrument: Mexameter MX18 (Courage & Khazaka). The study included several control visits: a visit before the beginning of treatment (T0), and a visit each week during the 4-week period. Photographs were taken at T0 and T4 using a numerical camera (Minolta dimage 7i). Cutaneous pigmentation change was evaluated through clinical observation as well as by quantification of the melanin index.

3. Results

Pigmentation change was measured by statistical treatment of the data and by quantification of the melanin index of the skin. The results are presented in the chart below.

Statistical analysis was carried out using the nonparametric Wilcoxon test for matched pairs, for each subject. Results were obtained using the following calculation:

$$\text{Score} = \text{Diff.} A_{/Un \text{ or } Pl} = T4\, A_{/Un \text{ or } Pl} - T0\, A_{/Un \text{ or } Pl}$$

A=Active ingredient; Un=Untreated; Pl=Placebo

Region of rejection: insofar as the direction of the difference is predictable, the region of rejection will be one-sided. The level of significance is $\alpha \leq 5\%$.

|  | Melanin Index | | | |
| --- | --- | --- | --- | --- |
|  | T0 | T4 | % of reduction | P |
| Active ingredient | 246.400 | 211.467 | −6.595 | 0.00235*** |
| Placebo | 237.333 | 236.267 | −0.449 | 0.4875[NS] |

***very significant
[NS]non-significant

These results showed that application of the active agent according to the invention considerably reduced the rate of melanin present in the skin. This reduction was observed particularly on hyperpigmented areas and after 4 weeks of application of the active agent, this reduction being statistically significant. In addition, these results were confirmed after clinical examination: 67% of the volunteers presented a reduction in the pigmentation of the area treated with the active agent compared to the area treated with the placebo. Moreover, a visible reduction in pigmentary marks was noted in 86% of the volunteers.

In conclusion, it was observed that the hydrolysate according to the invention, in a 3% gel formulation, has a depigmenting effect, i.e. a lightening effect on the skin as well as a genuine action in the fight against pigmentary marks.

EXAMPLE 4

Demonstration of the Effect of the Extract of Example 1 on Melanin Synthesis in Cultured Melanocytes 1. Determination of the Melanin Rate The principle of this test rests on a melanin assay using a spectrometric method.

"Diameter 60" culture dishes are seeded with $1.10^5$ cells, and then incubated for 24 hours. These cells, are then treated with the extract according to the invention, in 1%, 3%, or 7% solutions for 24 hours. The cells are then collected by trypsinization. Half of the cells is then used for the melanin assay and the other half for the determination of the protein content (using the Pierce technique). In order to carry out the melanin assay, the cells are solubilized in 1 ml of NaOH-1N/10%-DMSO for 2 hours at 80° C., then centrifuged for 10 minutes at 10000 g. The absorbance of the supernatant is then read at 470 nm and compared with the standard curve of the melanin. This standard curve is prepared with synthetic melanin (SIGMA) with concentrations between 0.05 and 100 μg/mL and with a final NaOH concentration of 0.2M.

Results are presented in the table below. The table presents the quantity of synthesized melanin, expressed in protein pg/μg, according to the various conditions of the studies.

|  | Conditions of the studies: | | | |
| --- | --- | --- | --- | --- |
|  | Controls | With extract at 1% | With extract at 3% | With extract at 7% |
| Amount of melanin (protein pg/μg). | 171 | 126 | 110 | 107 |

These results showed that the extract according to the invention makes it possible to significantly decrease the amount of melanin present in melanocytes, the extract acting in a dose-dependent manner.

2. Determination of Tyrosinase Activity

Tyrosinase is a key enzyme in the mechanism of melanin formation. The measurement of its activity makes it possible to determine the capacity of the active agent, according to the invention, to inhibit the mechanism of melanin formation. The principle of this test is based on a measurement of the oxidation rate of a substrate: L-dopa.

Cells are incubated in 6-well plates (with $1.10^5$ cells) for 24 hours. They are then treated with the extract according to the invention in a 3% solution for 24 hours, 48 hours, or 72 hours.

The cells are collected by trypsinization, rinsed 3 times with cold PBS, and then centrifuged for 5 minutes at 10000 g. The cells are lysed with 300 μL sodium phosphate buffer (0.1 M, pH 7) containing 1% X-100 triton+0.1 mm PMSF. After 30 minutes of incubation, the cellular extract is centrifuged at 10000 g for 10 minutes at 4° C., the supernatant is then collected. The protein content of each extract is determined by the Pierce technique. The L-DOPA is prepared at 2 mg/mL (10 mM) in a phosphate buffer (0.1 M; pH 7); a volume of 10 μL of each extract is placed in a 96-well plate and measurement of enzymatic activity is started by adding 100 μL of a L-DOPA solution at 37° C., and the "control" wells, containing 100 μL of lysis buffer, are carried out as well. The generation of the dopachrome is followed by absorbance measurement at 405 nm, every 10 minutes, for 1 hour, at 37° C. An absorbance curve is then established for each condition.

The final tyrosinase activity is presented in as A/min/g of protein according to the various conditions of the studies carried out. The results obtained are presented in the table below.

| Tyrosinase activity (A/min/g of protein) | Treatment for 24 h | Treatment for 48 h | Treatment for 72 h |
| --- | --- | --- | --- |
| Untreated cells | 130 | 83 | 54 |
| Treated cells | 124 | 74 | 46 |

These results enabled us to deduce that the extract according to the invention inhibits the activity of tyrosinase, a key enzyme in the mechanism of melanin formation, in a particularly effective way.

EXAMPLE 5

In Vitro Evaluation of the Whitening Effect of a Non Fermented Rapeseed Peptide Extract on the Skin Comparative studies were conducted using 1% of a non fermented rapeseed peptide hydrolysate for 72 hours, or 1% arbutin, known for its whitening effect, or a combination of both on ex vivo skin.

Skin biopsies are prepared as described in example 2. Four different conditions are tested:
   Condition 1: control, no active ingredient is applied
   Condition 2: Arbutin 1% is applied twice a day over a period of 72 hours
   Condition 3: non fermented rapeseed extract is applied twice a day over a period of 72 hours
   Condition 4: a combination of 1% of a non fermented rapeseed extract and 0.5% arbutin is applied twice a day over a period of 72 hours A quantitative evaluation of the presence of melanin in the epidermis of the skin samples is carried out histologically, under an optical microscope, using the Fontana-Masson staining method as described in example 2.

Results:

Both non fermented rapeseed extract and arbutin-treated skin exhibited a significant decrease in melanin content.

To confirm visual observations and quantify the results, image analysis was performed using several image processing steps and analysis of luminosity histograms. Histograms showing the results are presented in FIG. 1.

All date were normalized to the length of the basal layer within a given histological section. Table below shows the results obtained.

|  | Area under curve | Length of skin (micron) | Area/length (1/micron) | % of decrease |
|---|---|---|---|---|
| Control (Placebo) | 54517 | 816.39 | 66.78 | — |
| 1% arbutin | 46247 | 1015.73 | 45.53 | −31.8% |
| 1% non fermented rapeseed | 18820 | 553.96 | 33.97 | −49.1% |
| 1% non fermented rapeseed/0.5% arbutin | 31672 | 834.36 | 37.96 | −43.1% |

Normalized integrated values of histograms revealed a 49% decrease in melanin content in non fermented rapeseed extract-treated skin samples, compared to only 32% in arbutin-treated skin. Combination of the two products did not improve the rapeseed extract's whitening effect (−43%).

As a conclusion, the whitening effect of a non fermented rapeseed peptide hydrolysate is demonstrated. Moreover, the effects are superior to those obtained with arbutin.

EXAMPLE 6

Preparation of a Composition

The quantities indicated are expressed in weight percentages.

1—Complexion Enhancer Cream with Sun Protection:

| Commercial name | INCI name | w/w % |
|---|---|---|
| PHASE A | | |
| Montanov 68 | Cetearyl Alcohol (and) Cetearyl Glucoside | 5.00 |
| Isopropyl Palmitate | Isopropyl Palmitate | 7.00 |
| Waglinol 250 | Cetearyl Ethylhexanoate | 3.00 |
| Dow Corning 200 | Dimethicone Polydimethylsiloxane | 0.50 |
| Parsol MCX | Ethylhexyl Methoxycinnamate | 3.00 |
| Parsol 1789 | Butyl Methoxydibenzoylmethane | 1.00 |
| Phenonip | Phenoxyethanol (and) Methylparaben (and) Ethylparaben (and) Butylparaben (and) Propylparaben (and) Isobutylparaben | 0.50 |
| Cegesoft PS6 | Vegetable Oil | 2.00 |
| Jojoba oil | *Simmondsia Chinensis* (Jojoba) Seed Oil | 5.00 |
| PHASE B | | |
| Demineralised water | Aqua (Water) | qsp |
| Glycerin | Glycerin | 3.00 |
| Glucam E10 | Methyl Gluceth-10 | 0.50 |
| EDTA Tetrasodium | EDTA | 0.20 |
| PHASE C | | |
| Sepigel 305 | Polyacrylamide (and) C13-14 Isoparaffin (and) Laureth-7 | 0.35 |
| Lemon juice | *Citrus medica Limonum* (Lemon) Fruit Extract | 0.23 |
| PHASE D | | |
| Peptide hydrolysate as in example 1 | | 2.00 |
| Fragrance | Fragrance | qsp |
| Dye | Dye | qsp |

The components of phase A and phase B are heated at a temperature of 70° C., then phase A is emulsified in phase B. After emulsion, Sepigel is incorporated and then lemon juice. Phase D is then, added when the temperature is below 40° C.

The invention claimed is:

1. A topical skin and/or hair depigmenting and/or lightening composition, wherein the composition is applied to the surface of skin and/or hair of a person in need thereof, comprising an isolated rapeseed peptide hydrolysate fraction, wherein the isolated peptide hydrolysate fraction is solubilized in a cosmetically or pharmaceutically acceptable excipient selected from the group consisting of glycerol, propanediol and propylene glycol; and a cosmetic or dermatological medium comprising a fatty phase and emulsifiers or co-emulsifiers, wherein the isolated peptide hydrolysate fraction is present in an amount of 0.001% to 20% of the total weight of the composition, the fatty phase is present in an amount of 5% to 80% of the total weight of the composition, and the emulsifiers or co-emulsifiers are present in an amount of 0.3% to 30% of the weight relative to the total weight of the composition, and wherein the skin depigmenting and/or lightening composition is a water-in-oil emulsion, an oil-in-water emulsion or a combination thereof.

2. The composition of claim 1, wherein the isolated rapeseed peptide hydrolysate fraction is obtained from fermented or non-fermented rapeseed proteins.

3. The composition of claim 1, wherein the excipient is glycerol.

4. The composition of claim 1, wherein the isolated rapeseed peptide hydrolysate fraction contains peptide compounds in an amount between 30% and 90% of the total weight of the dry matter.

5. The composition of claim 1, wherein the isolated rapeseed peptide hydrolysate fraction contains 3.5 to 6 g/l of peptides and a concentration of sugars in an amount between 1 and 2 g/l.

6. The composition of claim 1, wherein the isolated rapeseed peptide hydrolysate fraction contains peptides with weights between 400 and 700 Da, and wherein the peptides are rich in proline amino acid.

7. The composition of claim 1, wherein the isolated rapeseed peptide hydrolysate fraction is obtained from non-fermented rapeseed proteins.

8. A method for depigmenting and/or lightening skin and/or hair in a person in need thereof comprising topically administering to skin and/or hair of said person, an effective amount of a composition comprising an isolated rapeseed peptide hydrolysate fraction solubilized in a cosmetically or pharmaceutically acceptable excipient selected from the group consisting of glycerol, propanediol and propylene glycol; and a cosmetic or dermatological medium comprising a fatty phase and emulsifiers or co-emulsifiers, wherein the isolated rapeseed peptide hydrolysate fraction is present in an amount of 0.001% to 20% of the total weight of the composition, the fatty phase is present in an amount of 5% to 80% of the total weight of the composition, and the emulsifiers or co-emulsifiers are present in an amount of 0.3% to 30% of the weight relative to the total weight of the composition, and wherein the skin depigmenting and/or lightening composition is a water-in-oil emulsion, an oil-in-water emulsion or a combination thereof.

9. The method of claim 8, wherein the rapeseed peptide hydrolysate fraction is obtained from non-fermented rapeseed proteins.

* * * * *